US012605419B2

(12) United States Patent
Sun et al.

(10) Patent No.: US 12,605,419 B2
(45) Date of Patent: Apr. 21, 2026

(54) FLAVONOID EXTRACT OF *CYCLOCARYA PALIURUS* LEAVES AND ANTIBACTERIAL DRUGS AND/OR ANTIBACTERIAL AGENTS CONTAINING THEREOF

(71) Applicants: WEST CHINA HOSPITAL, SICHUAN UNIVERSITY, Chengdu (CN); SICHUAN WANGE AGRICULTURAL TECHNOLOGY CO., LTD., Chengdu (CN)

(72) Inventors: Meiling Sun, Chengdu (CN); Jie Liu, Chengdu (CN); Wen Liao, Chengdu (CN); Minjun Liao, Chengdu (CN)

(73) Assignees: WEST CHINA HOSPITAL, SICHUAN UNIVERSITY, Chengdu (CN); SICHUAN WANGE AGRICULTURAL TECHNOLOGY CO. LTD., Chengdu (CN)

( * ) Notice: Subject to any disclaimer, the term of this patent is extended or adjusted under 35 U.S.C. 154(b) by 838 days.

(21) Appl. No.: 17/595,038

(22) PCT Filed: Aug. 20, 2020

(86) PCT No.: PCT/CN2020/110253
§ 371 (c)(1),
(2) Date: Nov. 5, 2021

(87) PCT Pub. No.: WO2021/196505
PCT Pub. Date: Oct. 7, 2021

(65) Prior Publication Data
US 2022/0305070 A1     Sep. 29, 2022

(30) Foreign Application Priority Data
Mar. 30, 2020     (CN) ......................... 202010239271.8

(51) Int. Cl.
*A61K 36/52* (2006.01)
*A61P 31/04* (2006.01)
(52) U.S. Cl.
CPC .............. *A61K 36/52* (2013.01); *A61P 31/04* (2018.01); *A61K 2236/331* (2013.01); *A61K 2236/333* (2013.01); *A61K 2236/37* (2013.01); *A61K 2236/39* (2013.01); *A61K 2236/51* (2013.01); *A61K 2236/53* (2013.01)

(58) Field of Classification Search
None
See application file for complete search history.

(56) References Cited

U.S. PATENT DOCUMENTS

2017/0173098 A1* 6/2017 Chen ...................... A01N 25/02

FOREIGN PATENT DOCUMENTS

CN        105395600 A      3/2016
CN        106381257 A      2/2017

OTHER PUBLICATIONS

Xie et al. (Extraction, chemical composition and antioxidant activity of Flavonoids from *Cyclocarya paliurus* (Batal.) Iljinskaja leaves, Food Chemistry, vol. 186, Nov. 1, 2015, pp. 97-105). (Year: 2015).*
Xie et al. (Extraction, chemical composition and antioxidant activity of Flavonoids from *Cyclocarya paliurus* (Batal.) Iljinskaja leaves, Food Chemistry, vol. 186, Nov. 1, 2015, pp. 97-105).*
Huang, Beibei et al.; Experimental Research on the Antibacterial Effect of Cyclocarya Paliurus, Journal of Jiangxi University of Traditional Chinese Medicine), vol. 18, No. 4, Aug. 31, 2006, pp. 48-49.
Yang, Wuying et al.; Study on the Purification of the Flavonoids from Cyclocarya paliurus with Polyamide Resin, Natural Product Research and Development, vol. 20, No. 2, Feb. 29, 2008, pp. 320-324.

* cited by examiner

Primary Examiner — Melissa S Mercier
(74) Attorney, Agent, or Firm — NKL Law; Allen Xue

(57) ABSTRACT

Flavonoid extract of *Cyclocarya paliurus* leaves is used in the preparation of antibacterial drugs and/or antibacterial agents against the bacteria that are resistant to conventional antibiotics. Experiments have proved that the flavonoid extract of *C. paliurus* leaves has obvious killing effect on methicillin-resistant *Staphylococcus aureus* strains, which provides a potential resolution to the problem that methicillin-resistant *S. aureus* strains are resistant to most beta-lactam antibiotics.

5 Claims, 2 Drawing Sheets

FLAVONOID EXTRACT OF *CYCLOCARYA PALIURUS* LEAVES AND ANTIBACTERIAL DRUGS AND/OR ANTIBACTERIAL AGENTS CONTAINING THEREOF

CROSS-REFERENCES TO RELATED APPLICATIONS

This application is a U.S. national phrase entry of PCT International Application No. PCT/CN2020/110253, filed Aug. 20, 2020, which claims the benefit of Chinese application No. 202010239271.8 filed Mar. 30, 2020, and entitled "USE OF THE FLAVONOID EXTRACT OF *CYCLOCARYA PALIURUS* IN PREPARATION OF ANTIBACTERIAL DRUGS AND/OR ANTIBACTERIAL AGENTS", which is herein incorporated by reference in its entirety.

TECHNICAL FIELD

The present invention belongs to the field of medicine, and specifically relates to the use of the flavonoid extract of *Cyclocarya paliurus* leaves in the preparation of antibacterial drugs and/or antibacterial agents against drug-resistant bacteria.

BACKGROUND TECHNOLOGY

Antibiotic resistance has become a major public health problem worldwide, and the abuse of antibiotics is one of the leading causes of antibiotic resistance. Methicillin-resistant *S. aureus* (abbreviated as "MRSA") developed resistance to multiple drugs and is accompanied by high morbidity and mortality. MRSA is one of the main pathogens causing necrotizing pneumonia, severe sepsis, necrotizing fasciitis, as well as one of the main pathogens causing hospital infections and community infections. Infections caused by MRSA bring great difficulties to clinical treatment. MRSA is resistant to most beta-lactam antibiotics or preparations, and even resistant to vancomycin, which is the most effective drug against the antibiotic resistant bacteria in clinical. Once MRSA progresses to completely resistant to vancomycin, the patients infected with MRSA will have no effective treatment available. Therefore, with the increasing challenge of antibiotic resistance, it is an urgent need to develop drugs to cope with the increasing antibiotic resistant.

*Cyclocarya paliurus* (Batal.) Iljinskaj a (*C. paliurus*) is a plant of *Cyclocarya* genus in Juglandaceae family, as a unique single genus. It is endemic in China and listed as an endangered tree species. *C. paliurus* is a tall and fast-growing broad-leaved tree. Because the tree shape resembles a willow, and the fruit is round like a copper coin and drooping, whose color is cyan, it is called "*C. paliurus*". According to the records of "Zhong Guo Zhong Yao Zi Yuan Zhi Yao", the leaves of *C. paliurus* have the functions of clearing heat, reducing swelling, and relieving pain, and can be used to treat stubborn ringworm. For a long time, the folks have used the leaves of *C. paliurus* to make tea, which has the effects of clearing away summer heat, lowering blood sugar level, controlling blood pressure, and prolonging the life.

At present, there are neither reports of using the extract of *C. paliurus* as a drug or preparation against drug-resistant bacteria, and nor demonstration that the extract of *C. paliurus* is used as a drug or preparation against MRSA.

CONTENT OF THE INVENTION

The object of the present invention is to provide a new use of the flavonoid extract of *C. paliurus* leaves in the preparation of antibacterial drugs and/or antibacterial agents against drug-resistant bacteria.

The present invention provides the use of the flavonoid extract from *C. paliurus* leaves in the preparation of antibacterial drugs and/or antibacterial agents, and the bacteria are drug-resistant. Further, the drug-resistant bacteria are drug-resistant gram-positive bacteria, preferably drug-resistant *S. aureus*, and more preferably MRSA.

Further, in said flavonoid extract of *C. paliurus* leaves, the content of the flavonoids is more than 50 wt. %, and preferably more than 67.3581 wt. %.

Further, said flavonoid extract of *C. paliurus* leaves is prepared by the following method: the leaves of *C. paliurus* are extracted with a solvent, and the extract solution is retained, which is then concentrated or dried, to provide the flavonoid extract.

Further, said leaves of *C. paliurus* are the dry powder of *C. paliurus* leaves; and/or, the solvent is water, and the mass ratio of the solvent to *C. paliurus* leaves is (5-15):1, preferably 10:1; and/or, the extraction temperature is 70° C. to 110° C., the extraction procedure are repeated 1 to 5 times, and the duration of extraction is 30 min to 120 min for each time. Preferably, the extraction temperature is 90° C., the extraction are 2 repeated procedures, and the extraction duration is 90 minutes for each extraction.

Further, before the extract solution is concentrated or dried, a purification process is also included, which comprises the following procedures:

Ethanol is added to the extract solution to make a final proportion of 50%-70%, and after mixing uniformly, the solution is centrifuged to retain the supernatant; preferably, the proportion of ethanol in the system is 60%.

Further, the purification also includes the following procedures: after removing the ethanol in the supernatant, the residue is loaded onto a polyamide resin column, and the column is eluted with water and 60% ethanol subsequently, where the amount of water is 5 BV, while the amount of 60% ethanol is 5 BV. The eluent is collected.

The present invention also provides a flavonoid extract of *C. paliurus* leaves, and said flavonoid extract of *C. paliurus* leaves is as described above.

The present invention further provides an antibacterial drug, which is prepared by using the flavonoid extract of *C. paliurus* leaves mentioned above as an active ingredient, with the addition of pharmaceutically acceptable excipients.

The present invention further provides an antibacterial agent, which is prepared by using the flavonoid extract of *C. paliurus* leaves mentioned above as an active ingredient, with the addition of excipients commonly used in the field of preparations.

Experimental results indicate that the flavonoid extract of *C. paliurus* leaves has obvious killing effect on MRSA strains, which provides a promising approach to deal with the challenge of increasing resistant to most antibacterial drugs. The flavonoid extract from *C. paliurus* leaves can be applied to preparation of antibacterial drugs or antibacterial agents against antibiotic-resistant bacteria, and have excellent application prospects in solving the worldwide problem of drug-resistant bacteria infection. Antibacterial drugs denote the drugs with bactericidal or antibacterial activity.

Antibacterial agents denote the preparations with bactericidal or antibacterial activity, and generally cannot be used to treat diseases.

The flavonoid extract of *C. paliurus* leaves denotes an extract containing flavonoids that is extracted from the leaves of *C. paliurus*. *C. paliurus* leaf flavonoids denote the flavonoids extracted from the leaves of *C. paliurus*. Flavonoids are a general term for a class of compounds with the structure of 2-phenylchromone (flavone).

Obviously, based on the above content of the present invention, according to the common technical knowledge and the conventional means in the field, without department from above basic technical spirits, other various modifications, alternations, or changes can further be made.

By following specific examples of said embodiments, the above content of the present invention is further illustrated. But it should not be construed that the scope of the above subject of the present invention is limited to following examples. The techniques realized based on the above content of the present invention are all within the scope of the present invention.

EXAMPLES

Figure 1:
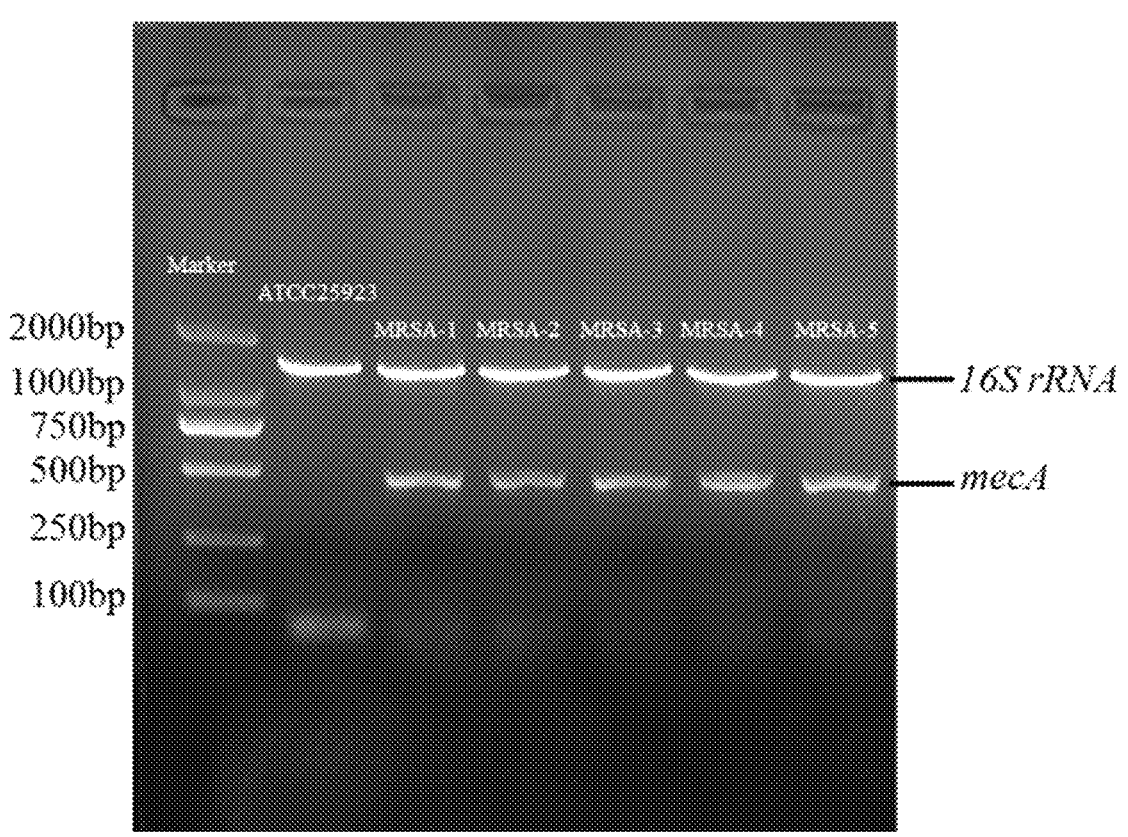
FIG. 1. The detection results of 16S RNA and mecA genes.

The starting materials and equipment used in the present invention are all known products and can be obtained by purchasing commercially available items.

Example 1 Preparation of the Flavonoid Extract of *C. paliurus* Leaves According to the Present Invention The *C. paliurus* leaves were dried in the shade at room temperature, and smashed. The smashed leaves (500 g) were soaked in 5 L water at 90° C. and maintained for 90 min. The supernatant was collected, and the residue was soaked in another 5 L fresh water at 90° C. to repeat the extraction procedure. The supernatant from both extractions were pooled and centrifuged to discard the precipitate, and concentrated. Ethanol was added in the concentrate to make a final concentration of 65% (v/v) ethanol. After mixing well, the suspension was centrifuged at 4800 r/min for 30 min. The supernatant was collected and the ethanol was removed until no alcohol can be smelled. The supernatant was loaded onto a polyamide resin column (the packing material is 100 g polyamide resin), and eluted with 5BV of water and 5BV of 60% ethanol subsequently. The eluate was collected. The ethanol in the collected eluate was recovered to obtain a fluid extract, which was dried in vacuum at 50° C. for 24 h until solid powder formed. This powder, namely the flavonoid extract from *C. paliurus* leaves, was weighed and stored for later use.

The content of flavonoids in this powder was quantitatively assessed using an ultraviolet-visible spectrophotometry following the General Rules 0401, Chinese Pharmacopoeia 2015 Edition, and with commercially available pure rutin as reference. Our assessment indicates the content of flavonoids is 67.3581 wt. %.

The beneficial effects of the present invention were demonstrated by the following experimental examples.

Experimental Example 1 the Bactericidal Effect of *C. paliurus* Leaf Flavonoids on MRSA 1. Strains and Drugs Strains: (1) *S. aureus* ATCC25923 was purchased from American Type Culture Collection (ATCC); (2) MRSA strains were isolated from West China Hospital, Sichuan University and provided by the Clinical Microbiology Laboratory: MRSA-1 (clinical number: 1911101191), MRSA-2 (clinical number: 1911081137), MRSA-3 (clinical number: 1911051296), MRSA-4 (clinical number: 1911051125), MRSA-5 (clinical number: 1911081165).

Drug: the flavonoid extract powder of *C. paliurus* leaves prepared in Example 1, penicillin sodium and oxacillin sodium (purchased commercially available products).

2. Cultivation of Bacteria

Medium: the culture medium for *S. aureus* ATCC25923, MRSA-1, MRSA-2, MRSA-3, MRSA-4, and MRSA-5 are Mueller-Hinton Broth (MHB).

Culture conditions: 37° C., 150 rpm shaker.

3. Experimental Methods 3.1 Identification of mecA Gene mecA gene is a specific drug-resistant gene of MRSA, which plays a decisive role in the antibiotic resistance of MRSA. In this experiment, PCR method was used to verify whether mecA gene exists in each strain. The specific method is as follows:

The bacterial genomic DNA extraction kit was used to extract the genomic DNA of each strain. The extraction procedures were performed according to the instructions of the kit. The genomic DNA of each strain was used as a template, and the 449 bp fragments of 16S RNA and mecA genes were amplified by a multiplex PCR technique. The primer sequence used is: 16S RNA upstream primer 5'-AGAGTTTGATCCTGGCTCAG-3' (SEQ ID NO.1) and downstream primer 5'-GGTTACCTTGTTACGACTT-3' (SEQ ID NO.2); mecA upstream primer 5'-CTCAGGTACTGCTATCCACC-3' (SEQ ID NO. 3) and downstream primer 5'-CACTTGGTATATCTTCACC-3' (SEQ ID NO. 4). The PCR amplification procedure is: 94° C. for 3 min, 94° C. for 45 s, 50° C. for 45 s, 72° C. for 1 min 30 s, 30 cycles, 72° C. for 5 min.

3.2 Experiment on the Sensitivity of Each Strain to Penicillin Sodium, Oxacillin Sodium and Flavonoids Extract of *C. paliurus* Leaves By referring to the methods and standards of the American Clinical and Laboratory Standards Institute (CLSI) for antimicrobial susceptibility testing, the drug resistance of each strain was verified. The MHB medium used in this test contained 2% NaCl (w/v).

Preparation of test bacteria: each bacterium was respectively inoculated in 5 ml MHB medium, and cultured overnight at 37° C. on a shaker. The bacterial solution was adjusted to 0.5 McFarland turbidity (MCF) unit, and further diluted by 100 folds. The final bacterial concentration was $5 \times 10^5$ cfu/ml.

Preparation of the flavonoids extract of *C. paliurus* leaves for application: 79.8 mg powder of the flavonoid extract from *C. paliurus* leaves prepared in Example 1 (based on the flavonoids proportion of 67.3581 wt. % in the flavonoids extract of *C. paliurus* leaves, the amount of flavonoids in the powder was 53.75 mg) was dissolved in 0.32 ml of DMSO, and further diluted with 3.68 ml MHB medium, to obtain the application solution of *C. paliurus* leaf with a flavonoids concentration at 13.44 mg/ml.

Preparation of the stock solution of penicillin sodium and oxacillin sodium: 100 mg of penicillin sodium or oxacillin sodium was dissolved in 1 ml of deionized water, and then filtered and sterilized through 0.22 μm filter membrane, to obtain the stock solution of penicillin sodium or oxacillin sodium. 10.24 μl stock solution of penicillin sodium or oxacillin sodium was transferred to 3.989976 ml of MHB media, to obtain 256 µg/ml application solution of penicillin sodium or oxacillin sodium.

Preparation of the flavonoid extract of *C. paliurus* leaves, penicillin sodium and oxacillin sodium solution in serial dilution: 100 µl application solution at the original concentration was added to the first and second wells of a 96-well plate. 100 µl of medium was added into the second well, and serial 2-fold dilutions were prepared until to the ninth well. The 10$^{th}$ well was set as the medium control. From the first hole to the ninth hole, the concentration of the flavonoid extract of *C. paliurus* leaves were 6720 µg/ml, 3360 µg/ml, 1680 µg/ml, 840 µg/ml, 420 µg/ml, 210 µg/ml, 105 µg/ml, 52.5 µg/ml, 26.25 µg/ml, respectively; the concentration of penicillin sodium or oxacillin sodium is 128 µg/ml, 64 µg/ml, 32 µg/ml, 16 µg/ml, 8 µg/ml, 4 µg/ml, 2 µg/ml, 1 µg/ml, and 0.5 µg/ml, respectively.

Sensitivity test: 100 µl of the bacterial solution prepared above was added to the wells with serial concentration of drugs and the medium control. The plate was placed in a humidified box and incubated at 34° C. for 24 hours. 20 µl of each bacterial solution was taken and diluted 50 times with the medium, then 100 µl of the diluted bacterial solution was spread on the culture plate and incubated overnight at 37° C. The minimum drug concentration without colony growth was determined as the minimum inhibitory concentration (MIC).

3.3 Experiment on the Bactericidal Effect of *C. paliurus* Leaf Flavonoids

None of the MHB medium used in this experiment was added with NaCl.

Preparation of test bacteria: same as described in 3.2.

Preparation of the application solution of the flavonoid extract of *C. paliurus* leaves: same as described in 3.2.

Preparation of the concentration gradient of the flavonoid extract of *C. paliurus* leaves: same as described in 3.2.

Test of bactericidal effect: 100 µl of the bacterial suspension prepared above was added to the wells with serial dilution of the flavonoid extract of *C. paliurus* leaves and the medium control. After mixing thoroughly, the plate was placed in a humidified box and incubated overnight at 37° C. 20 µl of each bacterial suspension was taken and diluted 10 folds with the MHB medium, then 100 µl of the dilution was spread on the culture plate and incubated overnight at 37° C. The number of colonies was counted.

Bactericidal rate=(1−the number of colonies in the drug group/the number of colonies in the medium control group)×100%

The minimum bactericidal concentration (MBC) of the drug was calculated by GraphPad Prism (Version 7.04) using nonlinear regression analysis. MBC$_{50}$ is the lowest concentration to reach 50% bactericidal effect.

4. Experimental Results 4.1 Detection of mecA Gene

As shown in FIG. 1, the expression of both 16S rRNA and mecA can be detected in all MRSA strains (MRSA-1, MRSA-2, MRSA-3, MRSA-4, and MRSA-5); the expression of only 16S rRNA was detected in common *S. aureus* ATCC25923. The results confirmed that the clinical isolates of MRSA used in this experiment were all methicillin-resistant, while *S. aureus* ATCC25923 was a sensitive strain to β-lactam drug.

4.2 Comparison of the Sensitivity of Various Strains to Penicillin Sodium, Oxacillin Sodium and *C. paliurus* Leaf Flavonoids As shown in FIG. 1, the sensitivity of each MRSA strain to penicillin sodium and oxacillin sodium was lower than that of the standard strain of *S. aureus* ATCC25923. The MIC value of each MRSA strain is 4 to 32 times that of *S. aureus* ATCC25923, or even higher. The sensitivity of each MRSA strain to *C. paliurus* leaf flavonoids is as the same as or higher than *S. aureus* ATCC25923. The results indicated that MRSA was not resistant to the antibacterial effect of *C. paliurus* leaf flavonoids.

TABLE 1

The MIC values of penicillin sodium, oxacillin sodium, and *C. paliurus* leaf flavonoids against each strain.

| Strains | MIC of penicillin sodium (µg/ml) | MIC of oxacillin sodium (µg/ml) | MIC of *C. paliurus* leaf flavonoids (µg/ml) |
|---|---|---|---|
| ATCC25923 | 0.03125 | 0.125 | 210 |
| MRSA-1 | 4 | 0.5 | 210 |
| MRSA-2 | 1 | 0.5 | 105 |
| MRSA-3 | 1 | 0.5 | 210 |
| MRSA-4 | 32 | >128 | 105 |
| MRSA-5 | 4 | 0.5 | 105 |

4.3 The Bactericidal Effect of *C. paliurus* Leaf Flavonoids

Figure 2:
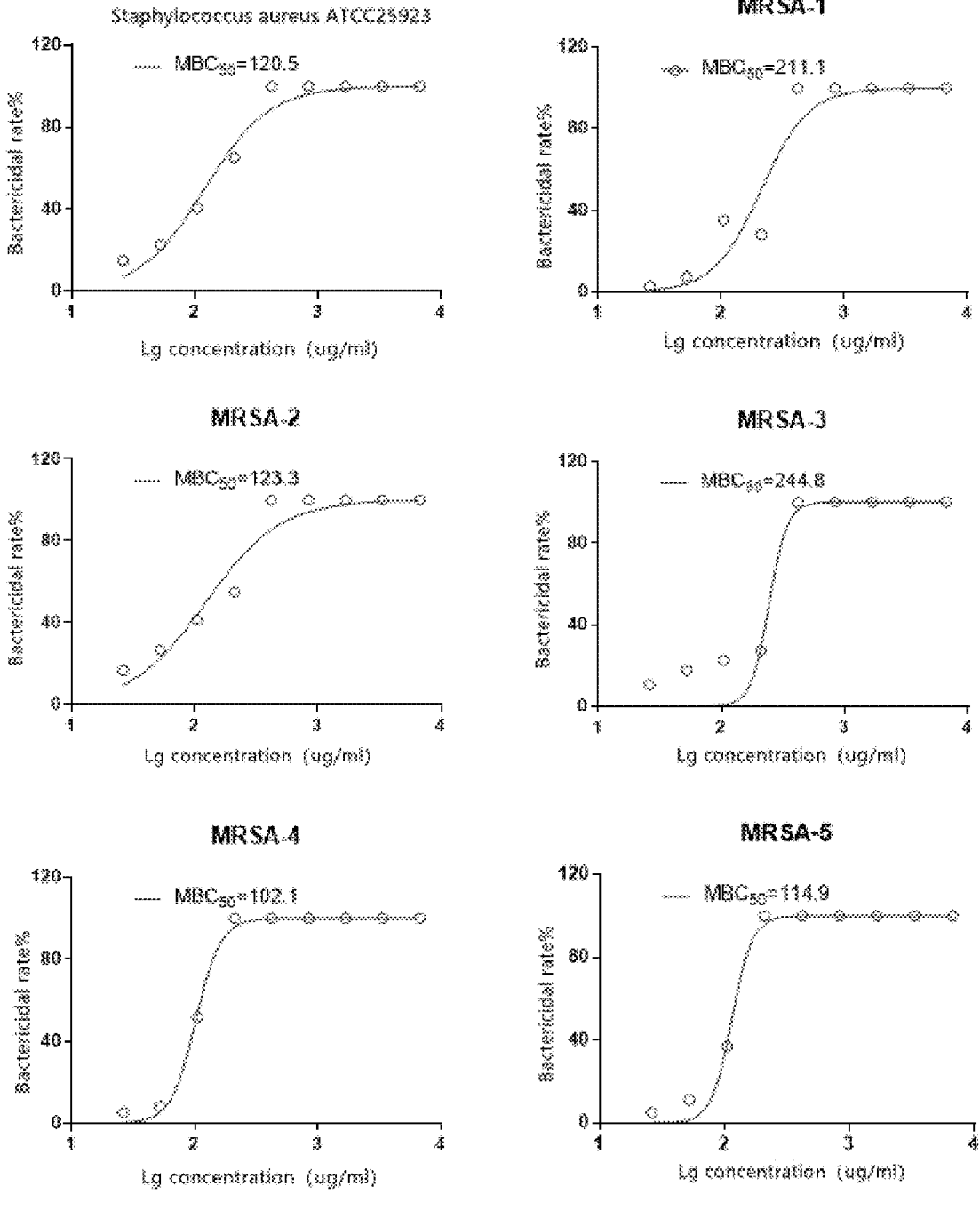
FIG. 2. The curve for the bactericidal effect of *C. paliurus* leaf flavonoids on various strains.

As shown in FIG. 2 and Table 2, *C. paliurus* leaf flavonoids not only had killing effect on *S. aureus* ATCC25923, but also had obvious killing effects on various MRSA strains, and the order of killing ability is: MRSA-4>MRSA-5>*S. aureus* ATCC25923>MRSA-2>MRSA-1>MRSA-3. Therefore, *C. paliurus* leaf flavonoids prepared in the present invention could effectively kill MRSA.

TABLE 2

MBC$_{50}$ values of *C. paliurus* leaf flavonoids against each strain.

| Strains | *C. paliurus* leaf flavonoids MBC$_{50}$ (µg/ml) |
|---|---|
| ATCC25923 | 120.5 |
| MRSA-1 | 211.1 |
| MRSA-2 | 123.3 |
| MRSA-3 | 244.8 |
| MRSA-4 | 102.1 |
| MRSA-5 | 114.9 |

In summary, the present invention provided a flavonoid extract from *C. paliurus* leaves, which had obvious killing effects on methicillin-resistant *S. aureus* strains, and overcome the problem that methicillin-resistant *S. aureus* strains were resistant to most antibacterial drugs. The flavonoid extracts of *C. paliurus* leaves could be prepared as antibacterial drugs or antibacterial agents against drug-resistant bacteria, and had excellent application prospects in solving the worldwide problem of drug-resistant bacteria infection.

The invention claimed is:

1. A method for treating drug-resistant bacteria, comprising administering a drug composition comprising a flavonoid extract of *Cyclocarya paliurus* leaves as an active ingredient and one or more pharmaceutically acceptable excipients, wherein the drug-resistant bacteria is drug-resistant *Staphylococcus aureus*.

2. The method according to claim 1, wherein the drug-resistant bacteria is methicillin-resistant *Staphylococcus aureus*.

3. The method according to claim 2, wherein a content of flavonoid in the flavonoid extract of *Cyclocarya paliurus* leaves is more than 50 wt. %.

4. A method for preparing a flavonoid extract of *Cyclocarya paliurus* leaves, comprising: mixing water and a powder of *Cyclocarya paliurus* leaves to form a first mixture at 70° C. to 110° C. for 30 min to 120 min;

separating the first mixture to obtain a first aqueous extract and a first solid;

mixing water with the first solid to form a second mixture at 70° C. to 110° C. for 30 min to 120 min;

separating the second mixture to obtain a second aqueous extract and a second solid; and concentrating the first extract and the second extract to obtain an extract solution;

adding ethanol to the extract solution to form a suspension in which ethanol is 50%-70% of a total volume;

centrifuging the suspension to obtain a supernatant;

removing ethanol in the supernatant to obtain a residue;

introducing the residue a polyamide resin column;

eluting the polyamide resin column first with water and then with 60% ethanol, wherein an amount of water is 5 bed volume (BV), and an amount of 60% ethanol is 5 BV, and collecting the elution.

5. The method according to claim 4, wherein a mass ratio of water to the powder of *Cyclocarya paliurus* leaves is (5-15):1.

\* \* \* \* \*